(12) United States Patent
Veriac et al.

(10) Patent No.: US 7,026,110 B1
(45) Date of Patent: Apr. 11, 2006

(54) REAGENT FOR DETERMINATION OF LEUCOCYTES AND MEASUREMENT OF HAEMOGLOBIN IN A SAMPLE OF BLOOD

(75) Inventors: Sylvie Veriac, Montpellier (FR); Henri Champseix, Montferrier sur Lez (FR)

(73) Assignee: Horiba ABX, Montpellier (FR)

( * ) Notice: Subject to any disclaimer, the term of this patent is extended or adjusted under 35 U.S.C. 154(b) by 0 days.

(21) Appl. No.: 09/527,028

(22) Filed: Mar. 16, 2000

(30) Foreign Application Priority Data

Mar. 19, 1999 (FR) .................................. 99 03467

(51) Int. Cl.
*A01N 1/02* (2006.01)

(52) U.S. Cl. .................... 435/2; 435/7.24; 436/522; 436/10; 436/17; 436/18; 436/63; 436/66; 436/164; 436/166; 436/172; 436/175; 436/176; 252/408.1

(58) Field of Classification Search ............... 436/8, 436/10, 17, 63, 66, 18, 172, 175, 164, 166, 436/176, 522; 435/2, 7.24; 252/408.1
See application file for complete search history.

(56) References Cited

U.S. PATENT DOCUMENTS

| | | | |
|---|---|---|---|
| 4,286,963 A | | 9/1981 | Ledis et al. |
| 4,617,275 A | | 10/1986 | Matsuda et al. |
| 4,983,375 A | | 1/1991 | Mauthner |
| 5,196,346 A | * | 3/1993 | Lefevre et al. ............... 436/63 |
| 5,389,549 A | * | 2/1995 | Hamaguchi et al. .......... 436/10 |
| 5,538,893 A | * | 7/1996 | Sakata et al. ................. 436/10 |
| 5,677,183 A | * | 10/1997 | Takarada et al. ............. 436/10 |
| 5,786,224 A | * | 7/1998 | Li et al. ....................... 436/63 |
| 5,935,857 A | * | 8/1999 | Riesgo et al. ................. 436/18 |
| 5,968,832 A | * | 10/1999 | Uchihashi et al. ............ 436/10 |

FOREIGN PATENT DOCUMENTS

| | | |
|---|---|---|
| EP | 0 177 137 | 4/1986 |
| EP | 0 444 240 | 9/1991 |
| EP | 0 695 936 | 2/1996 |

* cited by examiner

*Primary Examiner*—Long V. Le
*Assistant Examiner*—Gailene R. Gabel
(74) *Attorney, Agent, or Firm*—Connolly Bove Lodge & Hutz LLP

(57) ABSTRACT

The invention concerns a reagent for determination of leucocytes and measurement of haemoglobin in a sample of blood. This reagent comprises a buffer system that is suited to adjust selectively the pH of the reagent to an acidic value, at least one detergent of cationic type, a nitrogenous compound and, optionally, at least one inorganic salt. This reagent can be used in haematological analyses in human medicine and also permits the identification of a leucocytic subpopulation, in particular the basophil polymorphonuclear leucocytes.

11 Claims, 2 Drawing Sheets

REAGENT FOR DETERMINATION OF LEUCOCYTES AND MEASUREMENT OF HAEMOGLOBIN IN A SAMPLE OF BLOOD

BACKGROUND OF THE INVENTION

The invention relates to haematological analyses.

More particularly, it concerns a reagent for determination of leucocytes and measurement of haemoglobin in a sample of blood.

The invention also aims to provide such a reagent which permits a leucocytic subpopulation to be identified, in particular the basophil polymorphonuclear leucocytes.

The determination of leucocytes, in particular of certain leucocytic subpopulations, as well as the measurement of the haemoglobin concentration of the erythrocytes or red corpuscles are very important for diagnosis in human pathology.

It will be recalled here that the leucocytes, or human white corpuscles, are divided into five subpopulations, namely three main subpopulations: the lymphocytes, monocytes and polymorphonuclear leucocytes or granulocytes, with the latter being themselves subdivided into neutrophils, eosinophils and basophils, according to the characteristics of their cytoplasmic granules.

Determination of the total leucocytes as well as identification of their various subpopulations are achieved by means of traditional techniques of microscopic observation or by more modern techniques, mainly based on the measurement of variations in resistivity (WO 84/03771) or on optical diffraction (U.S. Pat. No. 3,740,143), which have been developed for specific automatic appliances.

For the identification of the leucocytic subpopulations the numeration of the basophil granulocytes is particularly tricky, considering that this population represents, in a healthy individual, only 0.5% to 1% of the total leucocytic population.

An increase in this basophil population is observed, attaining a population of 2 to 3% by weight, in the course of allergic reactions. Amongst the infections, tuberculosis and varicella can bring about basophilia, as can myxoedema and hyperlipidaemias amongst the metabolic diseases. Consequently, numeration of the basophil granulocytes assumes particular importance.

Patent FR 90 01660 and its equivalent U.S. Pat. No. 5,196,346 describe a reagent that preserves the basophil granulocytes in such a way so as to permit determination thereof by measurement of resistivity. However, this reagent does not permit the measurement of haemoglobin.

It will be recalled that haemoglobin is a chromoprotein contained in the red corpuscles of the blood or erythrocytes.

Measurement of the haemoglobin concentration therefore necessitates the use of a reagent for cellular lysis that is capable of causing lysis of the erythrocytes in order to liberate the haemoglobin for measurement thereof.

For this purpose it is known to use reagents containing at least one detergent and cyanide ions which are capable of carrying out conversion of the haemoglobin into a chromogenic compound in order to permit determination thereof by colorimetry measurement.

A cyanic reagent of this type is described in patents U.S. Pat. No. 3,874,852 and U.S. Pat. No. 3,854,914.

However, these reagents have the principal drawback of using cyanide. Moreover, they do not permit identification and quantification of the leucocytic subpopulations contained in the sample of blood to be analysed.

It should be noted that reagents that do not contain cyanide and that permit determination of leucocytes in addition to measurement of haemoglobin have already been proposed in the prior art.

Thus document WO 96/02841 describes a reagent for measuring haemoglobin without cyanide, which contains a detergent as well as a salt of hydroxylamine. This reagent can be used for numeration of the total leucocytes, but no leucocytic differentiation is possible.

Patent U.S. Pat. No. 5,242,832 describes a similar reagent which also permits partial leucocytic identification. However, this reagent does not permit identification of the basophil cells but permits solely evaluation of the lymphocytes, monocytes and granulocytes.

Document WO 98/32016 also describes a reagent of this type. However, the minority granulocytic subpopulations, namely the eosinophils and the basophils, are not identified by the reagent that is described in this publication.

SUMMARY OF THE INVENTION

The object of the invention is, notably, to overcome the drawbacks of the known reagents.

It aims, in particular, to provide a haematological-analysis reagent for the determination of leucocytes, and in particular for the identification and quantification of a leucocytic subpopulation constituted by the basophil cells, in a sample of whole blood.

The invention also aims to provide a reagent that permits, notably, lysis of the erythrocytes or red corpuscles, which is necessary for determination of leucocytes as well as for measurement of haemoglobin.

It also aims to provide such a haematological-analysis reagent in the form of a single reagent and not in the form of a system of reagents.

It aims, moreover, to provide such a haematological-analysis reagent that does not comprise cyanic compounds.

Furthermore, the invention aims to provide such a haematological reagent that is quite particularly suitable for automated haematological instruments.

To this end, the invention proposes a haematological-analysis reagent of the type defined above, which essentially comprises:

a buffer system that is suited to adjust selectively the pH of the reagent to an acidic value, in particular to a value lower than 3;

at least one detergent of cationic type; and a nitrogenous compound.

The buffer system of the reagent is a key constituent, for the pH of the reagent permits identification of the subpopulation constituted by the basophil cells, which are of particular interest.

In fact, on account of their biochemical characteristics the basophil cells are capable of resisting the aggressivity of an acidic pH for a longer time than the other leucocytic subpopulations. This property therefore permits their isolation and their identification, notably by a resistive measurement.

The buffer system is advantageously chosen so that the pH value of the reagent is lower than 3 and preferably equal to 2.4.

The buffer system is advantageously chosen from the following:

potassium chloride/hydrochloric acid;
tartaric acid/sodium hydroxide;
citric acid/sodium hydroxide;
potassium hydrogen phthalate/hydrochloric acid;

citric acid/disodium hydrogen phosphate; and boric acid/citric acid/potassium dihydrogen phosphate.

The detergents of cationic type fulfil a function of lysis of the red corpuscles or erythrocytes, permitting liberation of the haemoglobin, which afterwards can be determined by measurement of absorbance. Generally speaking, the ionic detergents (anionic and cationic) are mainly used in order to dissociate the proteinic complexes and to solubilise the proteins of the membranes. They are also known as denaturants. Their action is rapid and therefore compatible with the rate-constraints specific to automated instruments.

The detergent is advantageously chosen from the following compounds:

the primary amines, the acetates and hydrochlorides of fatty amines;

the quaternary ammonium salts and trimethylethylammonium bromide;

the amides of substituted diamines, cationised by ethyl sulfate, diethanolaminopropylamine or diethylaminopropylamide; and the amides of cyclised diethylenetriamine.

The nitrogenous compound essentially fulfils a function of physicochemical stabilisation of the by-products of oxidation of haemoglobin.

This nitrogenous compound is advantageously a thiourea, in particular 1,3-dimethyl-2-thiourea.

The reagent of the invention may comprise, moreover, at least one inorganic salt.

This salt, if it is present, intervenes in the detergent activity and permits the phenomena of osmosis at the level of the cellular membranes to be maintained within the limits of normality, which is important for determination of the basophil cells. This salt also plays a role in the methods for measuring resistivity which are generally applied in automated haematological instruments.

The inorganic salt is advantageously constituted by an alkali-metal salt. The chlorides or sulfates of sodium or potassium may principally be cited as usable salts.

In preferred manner the detergent is present in a concentration of 0.2–20 g/l and the nitrogenous compound is present in a concentration of 0.1–10 g/l.

DESCRIPTION OF PREFERRED EMBODIMENTS

The invention will now be described with reference to the following non-limiting example.

EXAMPLE

A haematological-analysis reagent is prepared from the compounds stated below and in the concentrations indicated:

| Compounds | Concentrations |
|---|---|
| potassium chloride | 5–10 g/l |
| 1,3-dimethyl-2-thiourea | 0.5–3 g/l |
| dodecyltrimethylammonium chloride | 0.5–5 g/l |
| potassium hydrogen phosphate/HCl | 1.0–10 g/l |

The above compounds are mixed, and the pH is adjusted to an acidic value lower than 3, typically of the order of 2.4.

With the aid of this reagent, haematological analyses are carried out in respect of a sample of whole human blood, using an automated haematology instrument.

In order to do this, 10 µl of the sample of whole blood are brought into contact with 2 µl of the above reagent at 35° C.

Various types of analysis are carried out by comparing the reagent of the invention with one or more reference reagents.

The reference reagent is a lysing agent which is used in automated haematological instruments in order to reproduce the dosage of haemoglobin according to the classical, non-automated methodology, so-called Drabkin methodology. It is a matter of the dosage of cyanomethaemoglobin.

According to this method, ferrous iron ($Fe^{++}$) of the haem of the haemoglobin, oxyhaemoglobin and carboxyhaemoglobin contained in the red corpuscles is oxidised to ferric iron ($Fe^{+++}$) by iron cyanide so as to form methaemoglobin. Methaemoglobin then combines with the cyanide ions so as to form cyanomethaemoglobin which is measured by spectrophotometry at 540 nm [Drabkin, J. Biol. Chem. 112:51 (1935)].

On the other hand, the reagent of the invention is used in a dosage mode without cyanide. The erythrocytic haemoglobin is eluted by the action of an appropriate lysis agent. The haemic iron of the eluted haemoglobin is oxidised by the combined action of the erythrocytolytic compound and of the oxygen which is dissolved in the solution. The free methaemoglobin is unstable in comparison with cyanomethaemoglobin. Use is therefore made of compounds having electron-donor atoms, in order to reduce the haemic iron and to stabilise the methaemoglobin.

The reagent of the invention is used for various types of analysis which are performed in an automated haematological instrument.

1) Numeration of the Leucocytes

A count of the total leucocytes or white corpuscles is carried out.

The results of measurement obtained with the reagent of the invention and those obtained with a reference reagent that does not permit even partial leucocytic differentiation are compared.

Figure 1:
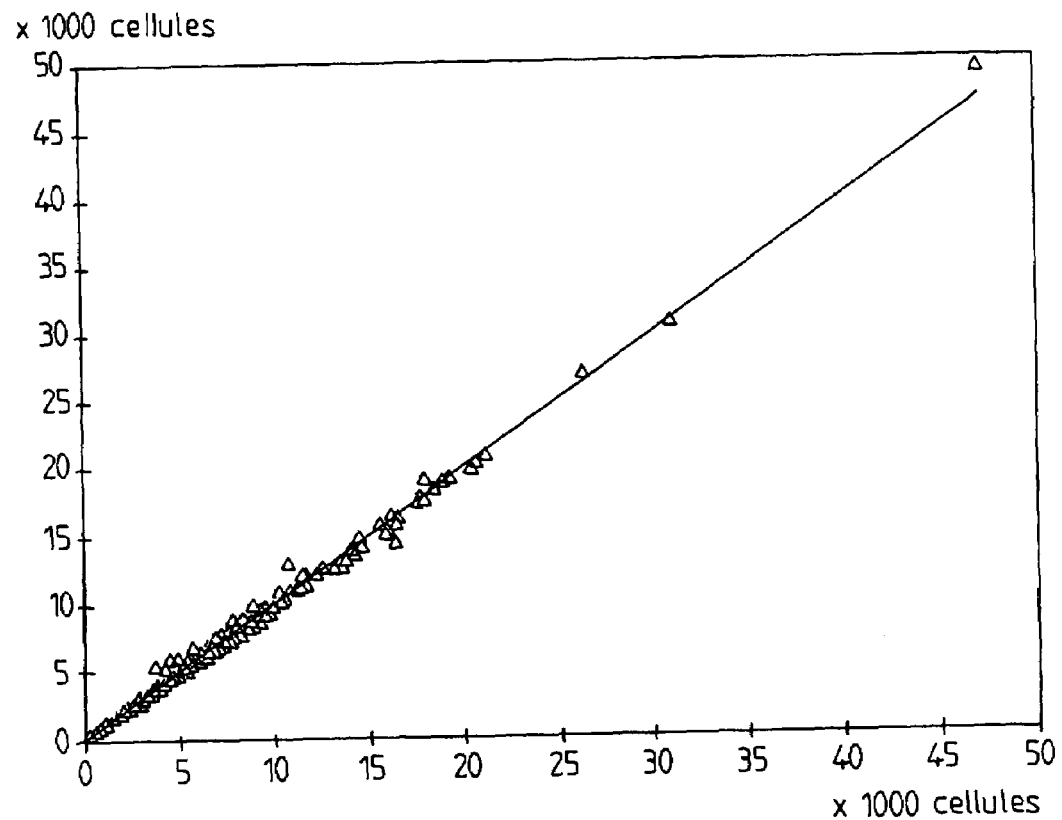
FIG. 1 is a graph showing values of measurements for the reagent of a preferred embodiment of the invention in comparison with a reference reagent.

FIG. 1 shows the values of measurements expressed in thousands of cells, on the one hand for the reference reagent which is represented on the abscissa, and on the other hand for the reagent of the invention which is represented on the ordinate.

The graph shows an excellent correlation between the two types of measurement. The values of the correlation coefficient ($R^2=0.99$) and of the slope of the straight regression line (0.99) indicate a very good correlation.

2) Differentiation and Numeration of the Basophil Polymorphonuclear Leucocytes

Figure 2:
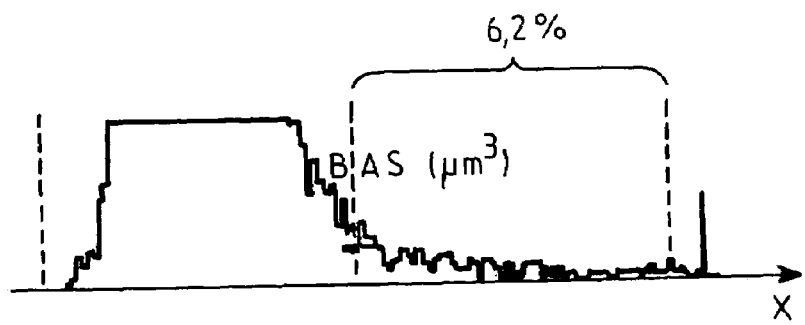
FIG. 2 is graph resulting from the reesistive analysis of a blood sample with a reagent according to the invention.

FIG. 2 shows the curve resulting from the resistive analysis of a sample of whole blood with the reagent of the invention that was described above. This curve represents a histogram of distribution of the cells according to their size.

The x-axis (abscissa) corresponds to the determination of the cellular volumes ($\mu m^3$) which are calculated by a resistive measurement. The basophil polymorphonuclear leucocytes are situated to the right of the central cursor (BAS). Located to the left of this central cursor are all the other leucocytic subpopulations, which cannot be differentiated volumetrically by reason of the high aggressivity of the pH of the reagent.

In the example, basophil polymorphonuclear leucocytes are identified which represent a proportion of 6.2% (by volume) in relation to the total leucocytic population.

3) Measurement of Haemoglobin

A measurement of haemoglobin is performed with the reagent of the invention, and the results of measurements of the haemoglobin concentration with the reagent of the invention and with a reference reagent containing cyanic compounds are compared.

Figure 3:
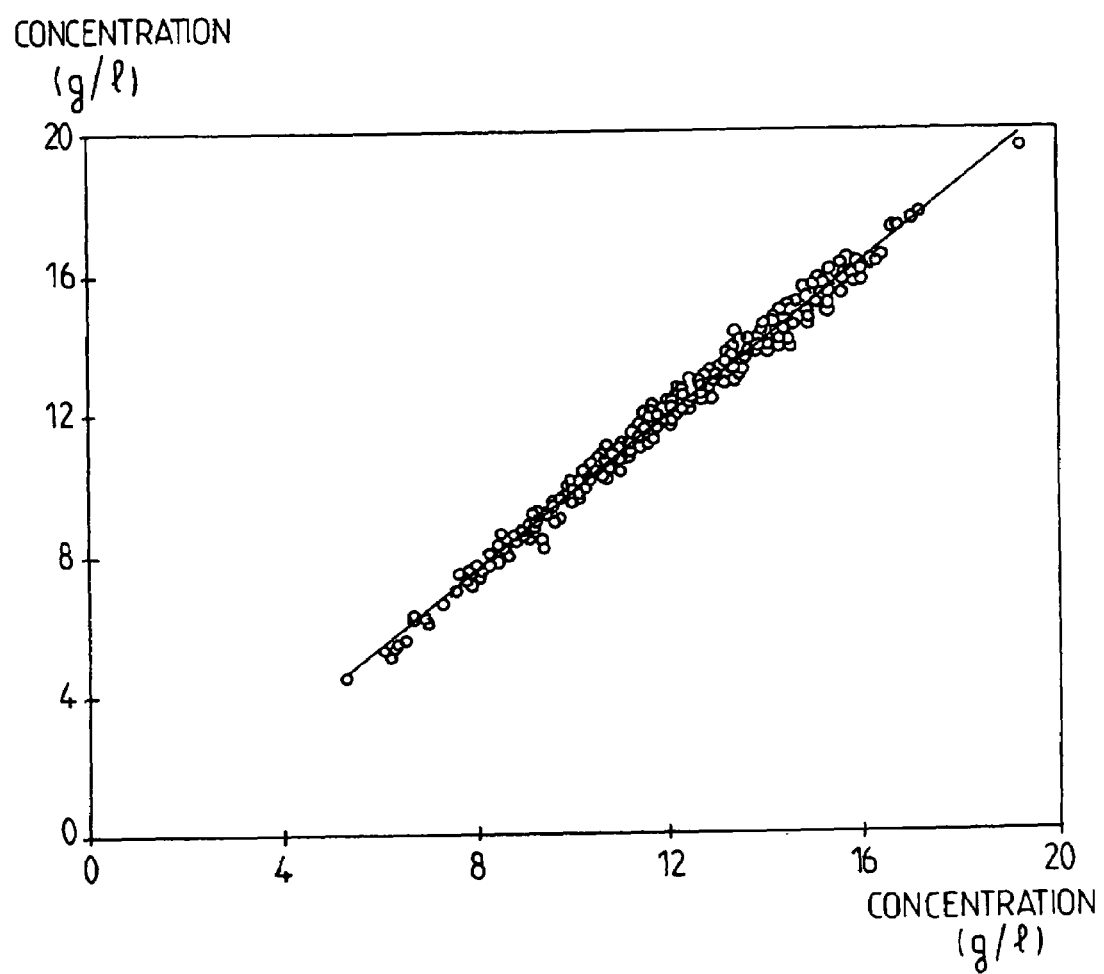
FIG. 3 is a graph showing the values of haemoglobin concentrations obtained by a reference reagent and by a reagent according to the invention.

FIG. 3 shows the values of haemoglobin concentrations (expressed in grams/liter) obtained by the reference reagent (representation on the abscissa) and by the reagent of the invention (representation on the ordinate). There too, the values of the correlation coefficient ($R^2=0.99$) and of the slope of the straight regression line (1.09) indicate a very good correlation.

Thus the invention provides a single reagent that permits determination of leucocytes, identification of a leucocytic subpopulation (in particular, the basophil polymorphonuclear leucocytes) and measurement of haemoglobin, without using cyanic compounds.

The reagent of the invention presents, notably, the distinctive feature of permitting measurement of haemoglobin under very acidic conditions in relation to the known reagents.

Furthermore, this reagent comes in the form of a single reagent and not in the form of a system of several reagents, and it is quite especially suitable for analyses that are performed in automated haematological instruments.

Of course, the invention is not limited to the embodiment example described previously but extends to other embodiment variants.

What is claimed is:

1. A single reagent for the simultaneous determination of total leucocytes, and basophile polymorphonuolear leucocytes, and for the measurement of hemoglobin in a sample of blood, said reagent comprising:
    a buffer suitable to adjust and maintain the pH to a value lower than 3;
    at least one cationic detergent;
    a nitrogenous compound, wherein said nitrogenous compound is a thiourea; and further comprising the absence of cyanic compounds.

2. The single reagent of claim 1, wherein said buffer adjusts the pH to a value of 2.4.

3. The single reagent of claim 1, wherein said buffer is a multi-component mixture selected from the group of mixtures consisting of:
    potassium chloride plus hydrochloric acid,
    tartaric acid plus sodium hydroxide,
    citric acid plus sodium hydroxide,
    potassium hydrogen phthalate plus hydrochloric acid,
    citric acid plus disodium hydrogen phosphate, and
    boric acid plus citric acid plus potassium dihydrogen phosphate.

4. The single reagent of claim 1, wherein said detergent is selected from the group consisting of primary amines, acetates of fatty amines, hydrochlorides of fatty amines, quaternary ammonium salts, trimethylethylammonium bromide, and amides of cyclized diethylenetriamine.

5. The single reagent of claim 1, wherein said detergent comprises amides of substituted diamines wherein said substituted diamines are canonized by a compound selected from the group consisting of ethyl sulfate, diethanolaminopropylamine, and diethylaminopropylamide.

6. The single reagent of claim 1, wherein said thiourea is 1,3-dimethyl-2-thiourea.

7. The single reagent of claim 1 further comprising at least one inorganic salt.

8. The single reagent of claim 7, wherein said at least one inorganic salt is an alkali metal salt.

9. The single reagent of claim 7, wherein said at least one inorganic salt is a chloride or sulfate of sodium or potassium.

10. The single reagent of claim 1, wherein said detergent is present at a concentration of 0.2–20 g/l and the nitrogenous compound is present at a concentration of 0.1–10 g/l.

11. The single reagent of claim 1 comprising:
    5–10 g/l potassium chloride;
    0.5–3 g/l 1,3-dimethyl-2-thiourea;
    0.5–5 g/l dodecyltrimethylammonium chloride; and
    1.0–10 g/l potassium hydrogen phosphate plus hydrochloric acid.

* * * * *